United States Patent
Pradhan et al.

(10) Patent No.: US 7,871,547 B2
(45) Date of Patent: Jan. 18, 2011

(54) HALIDE REDUCTION IN DIHYDROCARBYLMAGNESIUM MIXTURES

(75) Inventors: Milind M. Pradhan, Baton Rouge, LA (US); Chi Hung Cheng, Baton Rouge, LA (US); Rajeev S. Mathur, Baton Rouge, LA (US); Richard A. Holub, Baton Rouge, LA (US); Donald W. Imhoff, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 909 days.

(21) Appl. No.: 11/718,380

(22) PCT Filed: Nov. 12, 2004

(86) PCT No.: PCT/US2004/037822

§ 371 (c)(1),
(2), (4) Date: May 1, 2007

(87) PCT Pub. No.: WO2006/054967

PCT Pub. Date: May 26, 2006

(65) Prior Publication Data

US 2008/0023856 A1    Jan. 31, 2008

(51) Int. Cl.
C07F 1/02    (2006.01)
(52) U.S. Cl. .................................. 260/665 G
(58) Field of Classification Search .................. None
See application file for complete search history.

(56) References Cited

U.S. PATENT DOCUMENTS

| | | | |
|---|---|---|---|
| 3,646,231 A | 2/1972 | Kamienski et al. | |
| 3,766,280 A | 10/1973 | Kamienski et al. | |
| 4,069,267 A | 1/1978 | Kamienski et al. | |
| 4,299,781 A | 11/1981 | Fannin et al. | |
| 4,342,708 A | 8/1982 | Sakerai et al. | |
| 4,447,369 A | 5/1984 | Ashby | |
| 4,615,843 A | 10/1986 | Fannin et al. | |
| 4,678,614 A | 7/1987 | Kamienski et al. | |
| 5,015,750 A | 5/1991 | Tran et al. | |
| 5,145,600 A | 9/1992 | Kamienski et al. | |
| 5,626,717 A * | 5/1997 | Yin et al. ............... | 162/30.11 |
| 5,910,270 A | 6/1999 | Jones et al. | |

FOREIGN PATENT DOCUMENTS

DE    3229939 A1    2/1984
FR    2840901 A1    12/2003

OTHER PUBLICATIONS

Panwar et al., {Toxicity reduction of bleach plant effluent by using chemical additives, Ippta Journal (2004), 16(3), 45-52}.*
Desreumaux, Jacqueline, et al., "Reactions of Sodium-Potassium Alloys with Inert Gas Impurities—Potential Hazards after Oxidation," Eur. J. Inorg. Chem., 2000, pp. 2031-2045.
Glaze, et al., "The Preparation and Properties of Organomagnesium Copounds in Benzene Solvent", J. Organometallic Chem., 1966, vol. 5, pp. 477-480.
Grosse, et al., "Organolithium Compounds: I. Methods of Preparation", J. Org. Chem., 1940, vol. 5, pp. 106-121.
Hanawalt, Erin M., et al., "Organomagnesates from Reactions of Dialkylmagnesium Compounds with Alkali-Metal Alkoxides, Potassium Hydride, and Other Salts," Organometallics, 2004, vol. 23, pp. 416-422, Published on Web Jan. 7, 2004; plus Supporting Information, pp. S1-S12.
"High Surface Sodium," U.S. Industrial Chemical Co. Information Bulletin, 1953, 20 pages.
Malpass D. B., et al., "Preparation of Organometallic Complexes by Reduction of Magnesium Alkyls with Alkali Metals", J. Org. Chem., 1973, vol. 38, pp. 3718-3723.
Parris, G. E., et al., "The Composition of Grignard Compounds. VII. The Composition of Methyl- and *tert*-Butylmagnesium Halides and Their Dialkylmagnesium Analogs in Diethyl Ether and Tetrahydrofuran as Inferred from Nuclear Magnetic Resonance Spectroscopy", J. Am. Chem. Soc., 1971, 93:5 pp. 1206-1213.
Smith, Novis W., "Preparation of Organomagnesium Reagents in Hydrocarbon Solvents Without Organic Bases", J. Organometallic Chem., 1974, vol. 64, pp. 25-40.
Voltz, Sterling E., "The Catalytic Properties of Supported Sodium and Lithium Catalysts," J. Phys. Chem, 1957, vol. 61, pp. 756-758.
Wakefield, Basil J., "Organometallic Methods in Organic Synthesis", Academic Press, San Diego, 1995, pp. 3-8.

* cited by examiner

*Primary Examiner*—Daniel M Sullivan
*Assistant Examiner*—Chukwuma O Nwaonicha
(74) *Attorney, Agent, or Firm*—Jeremy J. Kliebert

(57) ABSTRACT

This invention provides a process for reducing the amount of soluble halide in a solution comprising a liquid organic medium, at least one viscosity reducing agent, at least one dihydrocarbylmagnesium compound, and an initial amount of soluble halide. The process comprises mixing at least one alkali metal with the solution at a mole ratio of alkali metal to magnesium of less than about 1:2.5, thereby forming precipitated soluble halides. Also provided by this invention is a process for reducing the amount of soluble halide in a slurry comprising a liquid organic medium, at least one viscosity reducing agent, at least one dihydrocarbylmagnesium compound, solids from the formation of said dihydrocarbylmagnesium compound, and an initial amount of soluble halide. This process comprises mixing at least one alkali metal with the slurry at a mole ratio of alkali metal to magnesium of less than about 1:1.25, thereby forming precipitated soluble halides.

39 Claims, No Drawings

HALIDE REDUCTION IN DIHYDROCARBYLMAGNESIUM MIXTURES

REFERENCE TO RELATED APPLICATION

This application is the National Stage of International Patent Appl. No. PCT/US2004/037822, filed on Nov. 12, 2004, the disclosure of which is incorporated herein by reference.

TECHNICAL FIELD

This invention relates to a process for reducing the amount of halide present in a solution or slurry comprising a dihydrocarbylmagnesium compound.

BACKGROUND

Solutions of dihydrocarbylmagnesium compounds are known to develop haziness over time. In dihydrocarbylmagnesium solutions, which are often viscous, the solids causing the haze settle very slowly. Haze formation has been ascribed to precipitation of dissolved chloride salts; thus, efforts have been made to remove these chloride salts from the dihydrocarbylmagnesium solutions. U.S. Pat. No. 4,615,843 discloses the use of alkyllithium compounds to reduce soluble chlorides. However, it was noted therein that care must be taken in order to minimize the amount of lithium in the solution, especially when a viscosity reducing agent is present in the solution with the dihydrocarbyl-magnesium compound, because the lithium from the alkyllithium compound may remain with the dihydrocarbylmagnesium compound.

The addition of alkali metals to dihydrocarbylmagnesium compounds in both solutions and slurries has been reported in the literature by Malpass and Eastham, *J. Org. Chem.*, 1973, 38, 3718-3723. The alkali metals were added to the dihydrocarbyl-magnesium compounds at a mole ratio of alkali metal to magnesium of about 1:1, with the alkali metal usually in excess relative to magnesium. The findings were that the stoichiometry of the reaction of the alkali metal with the dihydrocarbylmagnesium compound varied with the alkali metal used. Products having alkali metal, magnesium, and alkyl groups in varying proportions were formed. In many instances, precipitation of magnesium metal was observed.

SUMMARY OF THE INVENTION

The present invention provides processes for reducing the soluble halide in a dihydrocarbylmagnesium mixture. A wide range of stoichiometries of alkali metal may be used relative to the amount of soluble halide present to effect reduction of the soluble halide. A surprising advantage of the processes of the invention is that most of the alkali metal does not remain with the dihydrocarbylmagnesium mixture after the reduction of the soluble halide, contrary to the observations of Malpass and Eastham. In Malpass and Eastham's work, the alkali metal was observed to remain with the dihydrocarbylmagnesium compound, believed to be in the form of a hydrocarbylmagnesiumalkali metal complex. Underscoring the difference of the present processes from those of Malpass and Eastham is the observation in the present invention that the alkali metal appears to reduce the amount of trihydrocarbylaluminum compound (when such trihydrocarbylaluminum compound is the viscosity reducing agent, see below), without significantly affecting the amount of dihydrocarbylmagnesium compound present.

One embodiment of the invention is a process for reducing an initial amount of soluble halide in a solution comprising a liquid organic medium, at least one viscosity reducing agent, at least one dihydrocarbylmagnesium compound, and the initial amount of soluble halide. The process comprises mixing at least one alkali metal with the solution at a mole ratio of alkali metal to magnesium of less than about 1:2.5, thereby forming precipitated soluble halides.

Another embodiment of this invention is a process for reducing an initial amount of soluble halide in a slurry comprising a liquid organic medium, at least one viscosity reducing agent, at least one dihydrocarbylmagnesium compound, solids from the formation of the dihydrocarbylmagnesium compound, and the initial amount of soluble halide. The process comprises mixing at least one alkali metal with the slurry at a mole ratio of alkali metal to magnesium of less than about 1:1.25, thereby forming precipitated soluble halides.

Still another embodiment of this invention is a process which comprises a) forming, in a liquid organic medium, at least one dihydrocarbylmagnesium compound from at least one hydrocarbyl halide and magnesium metal, wherein optionally at least one viscosity reducing agent is present, resulting in a slurry comprising the liquid organic medium, the dihydrocarbyl-magnesium compound, solids from the formation of the dihydrocarbylmagnesium compound, and an initial amount of soluble halide;

b) removing the solids from at least a portion of the slurry formed in a), resulting in a solution comprising the liquid organic medium, the dihydrocarbylmagnesium compound, and the initial amount of soluble halide; and c) reducing the initial amount of soluble halide in at least a portion of the solution formed in b), in which at least one viscosity reducing agent is present, by mixing at least one alkali metal with the solution at a mole ratio of alkali metal to magnesium of less than about 1:2.5, thereby forming precipitated soluble halides.

Yet another embodiment of this invention is a process which comprises i) forming, in a liquid organic medium, at least one dihydrocarbylmagnesium compound from at least one hydrocarbyl halide and magnesium metal, wherein optionally at least one viscosity reducing agent is present, resulting in a slurry comprising the liquid organic medium, the dihydrocarbyl-magnesium compound, solids from the formation of the dihydrocarbylmagnesium compound, and an initial amount of soluble halide; and ii) reducing the initial amount of soluble halide in at least a portion of the slurry formed in i), in which at least one viscosity reducing agent is present, by mixing at least one alkali metal with the slurry at a mole ratio of alkali metal to magnesium of less than about 1:1.25, thereby forming precipitated soluble halides.

These and other embodiments and features of this invention will be still further apparent from the ensuing description and appended claims.

FURTHER DETAILED DESCRIPTION OF THE INVENTION

Throughout this document, the term "slurry" in reference to a slurry of a dihydrocarbylmagnesium compound means that solids from the formation of the dihydrocarbylmagnesium compound are present. Throughout this document, the term "solution" in reference to a solution of a dihydrocarbylmagnesium compound means that there are no solids from the formation of the dihydrocarbylmagnesium compound present, although other solids may be present in such a solution. As used throughout this document, the term "mixture," when referring to mixtures having dihydrocarbyl-magnesium compounds present, encompasses both solutions and slurries containing dihydrocarbylmagnesium compound(s).

The presence of oxygen and water in the practice of the present invention is usually detrimental. Thus, the minimization of oxygen and water in all manipulations is recommended and preferred. It is preferred that all operations are conducted in an inert atmosphere comprised of one or more inert gases, such as, for example, nitrogen, helium, or argon.

The liquid organic medium can be any liquid hydrocarbon, or a mixture of two or more hydrocarbons, which mixture is a liquid. The hydrocarbons are generally saturated or aromatic. Examples of suitable hydrocarbons include, but are not limited to, pentane, isopentane, cyclopentane, methylcyclopentane, hexane, isohexane, cyclohexane, methylcyclohexane, heptane, cycloheptane, octane, isooctane, cyclooctane, nonane, decane, benzene, toluene, xylene, mesitylene, ethylbenzene, diethylbenzene, 1,2,4-triethylbenzene, 1,3,5-triethylbenzene, amylbenzene, tetrahydronaphthalene, and the like. Preferred hydrocarbons are isopentane, isohexane, hexane, heptane, and toluene; more preferred are isopentane, isohexane, heptane, and toluene. When a particular hydrocarbon or mixture of hydrocarbons is desired to be used, a solvent swap may be performed, e.g., of a saturated hydrocarbon for an aromatic hydrocarbon. The presence of one or more ethers as part of the liquid organic medium is not desired or recommended in the practice of this invention.

As is known in the art, dihydrocarbylmagnesium mixtures tend to be very viscous, so at least one viscosity reducing agent is included in a dihydrocarbylmagnesium mixture. More than one viscosity reducing agent may be used in a dihydrocarbylmag-nesium mixture. Exemplary viscosity reducing agents include trihydrocarbylaluminum compounds, trihydrocarbylgallium compounds, and trihydrocarbylindium compounds. The hydrocarbyl groups in these compounds may be the same or different, and may be straight chain, branched, or cyclic. Examples of such viscosity reducing agents include trimethylaluminum, triethylaluminum, tri-n-propylaluminum, triisopropylaluminum, triisobutylaluminum, methyldiethylaluminum, diethylpentylaluminum, dimethylcyclo-hexylaluminum, trimethylgallium, triethylgallium, tri-n-propylgallium, triisobutylgallium, n-butyldiethylgallium, n-hexyldimethylgallium, tri-n-hexylgallium, dicyclohexylethyl-gallium, trimethylindium, triethylindium, tri-n-butylindium, tri-sec-butylindium, methyldicyclopentylindium, and the like. Trihydrocarbylaluminum compounds are preferred viscosity reducing agents. Preferred trihydrocarbylaluminum compounds are trimethylaluminum, triethylaluminum, tri-n-propylaluminum, triisopropylaluminum and triisobutylaluminum; more preferred are trimethylaluminum and triethylaluminum. A particularly preferred viscosity-reducing agent is triethylaluminum (TEA). A small amount of scrambling of the hydrocarbyl groups of the viscosity reducing agent with the hydrocarbyl groups of the dihydrocarbylmagnesium compound is occasionally observed. While the viscosity reducing agent is preferably present in an amount of about 1.5 to about 6.7 mole percent relative to magnesium (about 15 to about 67 moles of magnesium per mole of viscosity reducing agent), depending on the viscosity desired, deviations from these ranges are possible and within the scope of this invention.

Dihydrocarbylmagnesium compounds that may used in the invention include those in which each of the two hydrocarbyl groups is, independently, a primary hydrocarbyl group or a secondary hydrocarbyl group; the hydrocarbyl groups may be straight-chain, branched, or cyclic. The hydrocarbyl groups each contain from about one to about twenty carbon atoms. Preferably, each hydrocarbyl group has from two to about ten carbon atoms. Examples of dihydrocarbylmagnesium compounds include, but are not limited to, di-n-propylmagnesium, di-isopropylmagnesium, di-sec-butylmagnesium, dicyclopentylmagnesium, di-n-pentylmagnesium, di-n-hexylmagnesium, bis-(2-ethylhexyl)magnesium, dicyclohexylmagnesium, di-n-heptylmagnesium, di-n-octylmagnesium, methylnonylmagnesium, ethyl-n-hexylmagnesium, ethyldodecylmag-nesium, n-propylmethylmagnesium, n-butylmethylmagnesium, n-butylethylmagnesium, n-butyl-n-propylmagnesium, n-butylcyclopropylmagnesium, n-butyl-sec-butylmagnesium, n-butyl-n-hexylmagnesium, n-butyloctylmagnesium, methylisobutylmagnesium, ethylisobutylmagnesium, and the like. Preferred dihydrocarbylmagnesium compounds are n-butylethylmagnesium and n-butyloctylmagnesium. More preferred is n-butylethylmagnesium. The processes of the invention are also applicable to mixtures of dihydrocarbylmagnesium compounds. When the hydrocarbyl groups of the dihydrocarbyl-magnesium compound are different, or a mixture of dihydrocarbylmagnesium compounds is employed, a small amount of scrambling of the hydrocarbyl groups amongst the dihydrocarbylmagnesium compound(s) may be observed. The dihydrocarbylmagnesium compounds are in liquid form, either dissolved in a hydrocarbon solvent, or the dihydrocarbylmagnesium compound is in a molten state. If in the molten state, the dihydrocarbylmagnesium compound is dispersed in a liquid organic medium.

Various methods are known for preparing dihydrocarbylmagnesium compounds. In one such method, which is a preferred preparation method, magnesium metal and the appropriate hydrocarbyl halide(s) are combined in a liquid organic medium. Elevated temperatures are generally needed for the preparation, usually in the range of about 40° C. to about 100° C.; preferably, the temperature is at least about 60° C.; more preferably, the temperature is at least about 90° C. Byproducts of this preparation include magnesium halide and soluble halide. If a dihydrocarbylmagnesium compound having two different hydrocarbyl groups is desired, then two different hydrocarbyl halides are used. Optionally and preferably, a viscosity reducing agent is present during the preparation of the dihydrocarbylmagnesium compound. The liquid organic medium present during the preparation of the dihydrocarbylmagnesium compound may be the same as or different from the liquid organic medium present during the reduction of soluble halide. Preferably, the liquid organic medium for the preparation is a saturated hydrocarbon. For information on other methods of preparing dihydrocarbylmagnesium compounds, see U.S. Pat. No. 4,299,781 and references cited therein.

Solids, such as magnesium halides, which precipitate during the formation of the dihydrocarbylmagnesium compound can be removed by standard methods of solid-liquid separation, such as filtration. When the solids formed during the preparation of the dihydrocarbylmagnesium compound are removed by filtration prior to combination with an alkali metal, it is recommended and preferred that the filtration be conducted at elevated temperatures because elevated temperatures often decrease the viscosity of the mixture. Preferred elevated temperatures for filtering solids from the formation of the dihydrocarbylmagnesium compound from the slurry are in the range of about 40° C. to about 60° C. Alternatively, the slurry containing the precipitated solids from the formation of the dihydrocarbylmagnesium compound can be combined with alkali metal.

If a viscosity reducing agent is not present during the preparation of the dihydrocarbylmagnesium compound, it may be added at any point prior to the contacting of the dihydrocarbylmagnesium mixture with the alkali metal. Preferably, the viscosity reducing agent is made part of the mixture shortly after the preparation is finished, in order to ease further processing steps, such as the transfer of (at least a portion of) the mixture to another vessel and filtration. A highly preferred way of operating is to have a small amount of viscosity reducing agent present during the preparation of the dihydrocarbyl-magnesium compound, and to add more viscosity reducing agent after the preparation of the dihydrocarbylmagnesium compound.

The concentration of the dihydrocarbylmagnesium compound in the liquid organic medium can vary over a wide range. In general, viscosity increases with concentration. Thus, preferred concentrations of the dihydrocarbylmagnesium compound are in the range of about 0.2% to about 50% by weight. More preferably, the concentration is in the range of about 1% to about 30% by weight; even more preferably, the concentration of the dihydrocarbylmagnesium compound in the liquid organic medium is in the range of about 5% to about 25% by weight.

Soluble halide is usually present on the order of about 1000 ppm to about 2000 ppm at ambient temperatures in a 20 wt % dihydrocarbylmagnesium mixture, while at higher temperatures, the amount of soluble halide present is often greater. For example, at 80° C., a 20 wt % dihydrocarbylmagnesium mixture will often have about 2500 ppm soluble halide.

The soluble halide present with the dihydrocarbylmagnesium compound can be chloride, bromide, or iodide. Mixtures of two of these halides or all three of these halides may be present with the dihydrocarbylmagnesium compound. Occasionally, the soluble halide may be referred to as soluble halide ion or halide ion. In this document, the terms "soluble halide," "soluble halide ion," and "halide ion" are used interchangeably. Throughout this document, the term "soluble halide" is used to refer to dissolved halide species. Further, although analyses for halide ion suggest that the undesired species probably are halide ions, it is possible that the soluble halide may be in some other form. Regardless of its actual form, the dissolved species being reduced in the mixture is referred to as soluble halide, because of the familiarity of those of skill in this art with this terminology. Since the composition of the solid formed upon treatment with alkali metal is not known, the solid precipitate formed is referred to in this document as "precipitated soluble halide" or "precipitated soluble halides."

Without wishing to be bound by theory, the soluble halide is generally thought to be present as a byproduct of the synthesis of the dihydrocarbylmagnesium compound. Regardless of the source of the soluble halide present in the liquid organic medium with the dihydrocarbylmagnesium compound, the processes of the present invention may be used to reduce the amount of soluble halide present in the mixture. The presence of a large amount of soluble halide (usually on the order of greater than about 900 ppm, when measured as halide ion at ambient conditions) tends to cause hazing of the liquid organic medium over time, as the soluble halide slowly precipitates.

The amount of soluble halide removed from the dihydrocarbylmagnesium mixture is not always directly proportional to the amount of alkali metal used. Other variables, such as temperature, affect the extent of reduction of soluble halide. To calculate the amount of alkali metal relative to soluble halide, the amount of soluble halide present in the dihydrocarbylmagnesium mixture can be determined by known analytical methods, such as silver nitrate titration. Mole ratios of alkali metal to soluble halide are usually different for a dihydrocarbylmagnesium solution than for a dihydrocarbylmagnesium slurry. For solutions, the mole ratio of alkali metal to the initial amount of soluble halide is usually no more than about 10:1, while for slurries, the mole ratio of alkali metal to the initial amount of soluble halide is normally no more than about 20:1. While it is possible to work at mole ratios of alkali metal to soluble halide that are greater than 10:1 for dihydrocarbylmagnesium solutions, doing so is not necessary in order to achieve nearly complete reduction of the soluble halide. When the dihydrocarbylmagnesium mixture is a slurry, preferred mole ratios of alkali metal to soluble halide are in the range of about 6:1 to about 12:1. If the dihydrocarbylmagnesium mixture is a solution, the mole ratio of alkali metal to soluble halide is preferably in the range of about 0.5:1 to about 5:1; more preferred is a mole ratio is in the range of about 0.75:1 to about 3.5:1. It is preferred to mix alkali metal with dihydrocarbylmagnesium solutions, even though this adds an extra separation step, because of the lesser amount of alkali metal needed.

The alkali metals that can be used in the practice of the invention include lithium, sodium, potassium, rubidium, and cesium. Sodium and potassium are preferred alkali metals. Sodium is more preferred when only one alkali metal is used. The alkali metal can be used as a solid, as a dispersion in a liquid, or on a support. When more than one alkali metal is used, the metals may be combined with the dihydrocarbylmagnesium mixture separately, or the alkali metals may be premixed before being combined with the dihydrocarbylmagnesium mixture. Premixing of the alkali metals is preferred; a highly preferred mixture of alkali metals is sodium potassium alloy, sometimes referred to as NaK. For mixtures of alkali metals, the alkali metals can be in any desirable proportion to one another. When sodium potassium alloy is used as the mixture of alkali metals, preferred ratios of sodium to potassium are in the range of about 10:90 to about 60:40 wt/wt. More preferred ratios of sodium to potassium are in the range of about 20:80 to about 40:60 wt/wt. NaK, when the potassium content is about 40 wt % to about 90 wt %, is a liquid at ambient temperatures (~25° C.), and is in a convenient form to use.

Suitable liquids for alkali metal dispersions include liquid hydrocarbons such as those listed for the liquid organic medium above, and mineral oil. Support materials for alkali metals are generally any finely divided inorganic solid support, such as talc, clay, silica, alumina, silica-alumina, or mixtures thereof, and diatomaceous earth may also be used as a support material, alone or in combination with one or more finely divided inorganic solid supports. Other suitable support materials include carbon, soda ash, sodium carbonate, and silicon carbide. Preferred support materials are inorganic particulate solid catalyst supports or carrier materials such as inorganic oxides, aluminum silicates, or inorganic compositions containing inorganic oxides, such as kaolinite, attapulgite, montmorillonite, illite, bentonite, halloysite, similar refractory clays, and diatomaceous earth. Inorganic oxides that may be employed either alone or in combination with silica, alumina, or silica-alumina are magnesia, titania, zirconia, and the like. More preferred as support materials are silica, alumina, silica-alumina, and diatomaceous earth. The inorganic oxides may be, and preferably are, dehydrated to remove water, due to the water-reactive nature of alkali metals. Optionally, the residual surface hydroxyl groups in the inorganic solid porous support may be removed by additional heating or by reaction with chemical dehydrating agents such as lithium alkyl, silylchloride, or aluminum alkyls. For further information on alkali metal on supports see Voltz, *J. Phys. Chem.*, 1957, 61, 756-758, and *High Surface Sodium*, bulletin, U.S. Industrial Chemicals Co., New York, N.Y., 1953.

The mole ratio of alkali metal to magnesium for solutions is less than about 1:2.5. Preferably, for solutions, the amount of alkali metal used is at least about ten times less than a stoichiometric amount of alkali metal relative to the dihydrocarbylmagnesium compound. For slurries, the mole ratio of alkali metal to magnesium is less than about 1:1.25. When working with amounts of alkali metal that are about four or five times less than the molar amount of magnesium, adverse effects are not normally observed.

Generally, the order of addition is not important; however, due to the small amount of alkali metal used relative to the amount of dihydrocarbylmagnesium mixture, it is usually more practical to add the alkali metal to the dihydrocarbylmagnesium mixture. The alkali metal may be combined with the dihydrocarbylmagnesium mixture all at once or over a period time. It is recommended and preferred to stir the mixture for a period of time after the alkali metal and the dihydrocarbylmagnesium mixture have been combined to ensure good mixing of the alkali metal in the liquid organic medium, and to thus maximize the reduction of soluble halide. Typical post-combination stirring times on the laboratory scale are on the order of about 45 minutes to about four hours, while on the plant scale, typical post-combination stirring times are often about one hour to about ten hours.

Ambient conditions (~20-25° C.) are normally suitable for the mixing of the alkali metal and the dihydrocarbylmagnesium compound. Operation at elevated temperatures is feasible. Suitable temperatures are in the range of about 0° C. to about 150° C. Preferred elevated temperatures for dihydrocarbylmagnesium solutions are in the range of about 20° C. to about 110° C., while preferred elevated temperatures for dihydrocarbylmagnesium slurries are in the range of about 40° C. to about 60° C.; for slurries it is more preferred to work at ambient conditions because the amount of soluble halide increases as the temperature of the slurry increases. Since the processes can be conducted at pressures above atmospheric, some of the higher temperatures are achieved under superatmospheric pressure. The upper temperature suitable in any given procedure is that which gives reduction of soluble halide without deleterious effects upon the dihydrocarbylmagnesium compound, such as decomposition.

The processes of the invention reduce soluble halides in the liquid organic medium by causing the soluble halides to precipitate as solids. Separation methods that are well known in the art may be used for effecting the separation of the precipitated solids from the liquid organic medium, such as filtration or centrifugation. For a dihydrocarbyl-magnesium slurry, the precipitated soluble halides can be separated along with the solids from the formation of dihydrocarbylmagnesium compound in a single step.

Filtration at elevated temperatures is sometimes desirable because of the decreased viscosity of the mixture at such elevated temperatures. While the decreased viscosity at elevated temperature is an advantage, for a slurry, the amount of soluble halide present is increased at elevated temperatures. Thus, when a slurry is to be filtered at an elevated temperature to take advantage of reduced viscosity, an additional amount of alkali metal is usually needed to precipitate the greater amount of soluble halide present. When a dihydrocarbylmagnesium slurry that has been combined with alkali metal is filtered at an elevated temperature, it is recommended and preferred that the mixing with alkali metal, or at least stirring of the mixture after such mixing, is conducted at an elevated temperature prior to filtration. In contrast to dihydrocarbylmagnesium slurries, the amount of soluble halide present in a dihydrocarbylmagnesium solution does not increase at elevated temperatures. A preferred way of operating when the mixture is relatively viscous (e.g., viscous enough to cause handling difficulties) is to filter the solids from the formation of the dihydrocarbylmagnesium compound from the slurry at an elevated temperature, combine the resultant dihydrocarbylmagnesium solution with alkali metal, and filter the solution that contains the precipitated soluble halides at an elevated temperature.

When filtration is the method for solid-liquid separation, filter aids may be used, and their use is preferred. Suitable filter aids include diatomaceous earth, charcoal, and activated carbon; diatomaceous earth is preferred. A preferred method is to coat the filter with the filter aid prior to filtration of the dihydrocarbylmagnesium mixture. A preferred method for coating the filter is to suspend the filter aid in a liquid medium or in a previously filtered dihydrocarbylmagnesium mixture, and to pass this mixture through the filter at least once, and preferably until a clear filtrate is obtained, which may require additional filtrations through the same filter.

Use of either a support for the alkali metal or a filter aid is preferred and highly recommended. It has been found that the use of a filter aid, particularly with sodium potassium alloy in liquid form, helps prevent agglomeration of the alkali metal (s). The use of both a support for the alkali metal and a filter aid is possible in the practice of this invention, but is not considered necessary for the achievement of good results.

Generally, the processes of the invention reduce the soluble halide in the dihydrocarbylmagnesium mixture by at least about 25%. In the practice of the invention, nearly complete removal of the halide ion has been achieved. Surprisingly, it has been found that, after separation of precipitated soluble halides, relatively low amounts of alkali metal remain in the dihydrocarbylmagnesium solution, e.g., on the order of less than about 50 ppm. Often, even lower amounts of alkali metal remain, on the order of less than about 25 ppm, or sometimes even less than about 10 ppm. This low amount of alkali metal is seen irrespective of the amount of alkali metal used relative to the soluble halide.

While it has been found possible to reduce soluble halides in the presence of large amounts of precipitated magnesium halide (i.e., a slurry), this precipitated halide returns to solution over time, sometimes before the separation of the precipitated soluble halide from the slurry is complete. After two hours, the reduction in the amount of soluble halide appears unchanged from the initially observed reduction; however, after about twenty-four hours, significant amounts of the precipitated soluble halides have been observed to have returned to the liquid portion of the dihydrocarbylmagnesium slurry (i.e., the precipitated soluble halides are redissolved). Thus, it is often preferred to reduce the soluble halide in dihydrocarbylmagnesium solutions, even though this usually requires an extra solid separation step.

The presence of a viscosity reducing agent in the dihydrocarbylmagnesium mixture does not appear to have an adverse effect on the ability of the alkali metal to reduce soluble halide. Unexpectedly, it has been observed that, under certain conditions, at least in the case of trihydrocarbylaluminum compounds, their concentration in the dihydrocarbylmagnesium mixture is also reduced by the alkali metal. In particular, it has been found that, for dihydrocarbylmagnesium solutions, when the mole ratio of alkali metal to soluble halide used is at least about 0.75:1, a small reduction (about 10% or less) in the amount of the trihydrocarbylaluminum compound in the mixture is observed. With mole ratios greater than about 1:1, increased reduction in the amount of the trihydrocarbylaluminum compound is seen for solutions; see Examples 4 and 5 below. Little if any reduction in the amount of the trihydrocarbylaluminum compound is observed in solutions when the alkali metal to soluble halide mole ratio is about 0.75:1 or less. Analogously for dihydrocarbylmagnesium slurries, when the mole ratio of alkali metal to soluble halide used is at least about 7.5:1, a small reduction in the amount of the trihydrocarbylaluminum compound in the mixture can be observed; see Example 9 below. For mole ratios greater than about 9:1, increased reduction in the amount of the trihydrocarbylaluminum compound is sometimes observed for slurries; see Examples 10 and 11 below. Reactions of alkali metals with trihydrocarbylaluminum compounds have been reported; see U.S. Pat. No. 5,015,750, and Grosse and Mavity, *J. Org. Chem.*, 1939, 5, 106-121.

Without wishing to be bound by theory, it is thought that the alkali metal reacts preferentially with the soluble halide, and then some of the remainder of the alkali metal reacts with the trihydrocarbylaluminum compound in preference to reacting with the dihydrocarbylmagnesium compound; see Examples 10 and 11 below. It is expected that a similar effect (as to reduction in amount) should be observed for trihydrocarbylgallium compounds and trihydrocarbylindium compounds, when they are used as viscosity reducing agents.

The following examples are presented for purposes of illustration, and are not intended to impose limitations on the scope of this invention. While most of the Examples illustrate the practice of this invention for relatively high amounts of soluble halide, the processes of the invention may be practiced on dihydrocarbylmagnesium mixtures having a much lower amount of soluble halide.

EXAMPLES

General Procedures

Reagents. The butylethylmagnesium used in the following examples was prepared from n-butyl chloride, ethyl chloride, and magnesium metal. Triethylaluminum was present in all of the butylethylmagnesium solutions and slurries in the Examples below. The filter aid used in all of the Examples was diatomaceous earth (Hyflo Super-Cel®; World Minerals, Inc.), referred to herein as Hyflo. In all of the butylethylmagnesium slurries, bulk $MgCl_2$ was present, while in all of the butylethylmagnesium solutions, bulk $MgCl_2$ had been removed by filtration. Where a filter screen was used, a 24×110 Dutch weave screen was employed.

Analyses. In all of the following Examples, the amount of chloride present was determined by titration with silver nitrate, and is reported as chloride ion in parts per million. Samples for analysis were filtered through a syringe with a PTFE (polytetrafluoroethylene) filter disk when the sample was from a slurry, and/or when no filter aid was used. Where reported, the Na and/or K levels were determined by ICP. The relative amounts of Al and Mg were determined by measuring the $^1$H NMR resonances on the respective metals.

Conditions. All manipulations were conducted under $N_2$ (glove box or Schlenk line) with $H_2O$ and $O_2$ levels under 2 ppm. Filtration in all of the Examples, except for analytical samples, was carried out using a Mott filter assembly. The Mott filter assembly is a 6.0 cm (2-⅜-inch) diameter, pressure-rated metal cylinder with a metal screen at the bottom. Material to be filtered was introduced at the top, the cylinder was closed using tri-clover clamps, and the material was filtered by applying pressure to the cylinder.

Example 1

All filtrations in this Example used 0.5 micron PTFE filter membranes. In a dry box, a magnetic stir bar was placed in a flask, which flask was placed in a mineral oil bath. A butylethylmagnesium slurry in heptane (41.19 g, ~10% butylethylmagnesium) was added to the flask, and heated to 82° C., and then cooled to 50° C. The agitation was turned off, the solids in the slurry were allowed to settle, and 4.2 g of the supernatant was filtered for analysis. The butylethylmagnesium solution contained 964 ppm chloride and 1.3 ppm Na. Stirring of the slurry was resumed, and 0.07 gm of 30% Na in heptane was added. After stirring for 17 minutes, the agitator was turned off, and the solids were allowed to settle out of the solution while the temperature was maintained at 50° C. The supernatant of the slurry was filtered, analyzed, and found to have 617 ppm $Cl^{\ominus}$ and 10 ppm Na. Conditions and results are summarized in Table 1.

Example 2

A slurry of butylethylmagnesium in isohexane (12.6 g, 20%) was analyzed for chloride (1177 ppm), and then the slurry was transferred into a bottle. While stirring at ambient temperature, a Na dispersion in toluene (0.08 g; 30 wt % sodium) was added to the butylethylmagnesium slurry. Stirring was continued for 4 hours. The slurry was then filtered. The filtrate was analyzed for $Cl^{\ominus}$ content. Conditions and results are summarized in Table 1.

Example 3

In a dry box, a solution of butylethylmagnesium (10%) in heptane was filtered through a 0.5 μm PTFE filter membrane. The filtrate was analyzed and found to contain 616 ppm of chloride, 10.28% butylethylmagnesium, and 1.87 mole % Al, relative to Mg. The filtrate (11.67 g) was added to a sample vial. A sodium dispersion in toluene (0.02 g; 30 wt % sodium; moles Na:$Cl^{\ominus}$=1.3:1) was added, with stirring, to the butylethylmag-nesium solution (the filtrate) at room temperature. The solution was filtered at room temperature and analyzed, and found to have 442 ppm of chloride ion. Conditions and results are summarized in Table 1.

Example 4

A solution of butylethylmagnesium in heptane (12 g, 20%) was treated as described in Example 2; 0.105 g of the Na dispersion in toluene was used, and the slurry was stirred was for 3 hours. The initial Mg to Al mole ratio was 18.5:1 (5.4 mole % Al); the final Mg to Al mole ratio was 33.9:1 (3 mole % Al). In the final solution, the amount of Na was 10 ppm. Conditions and results are summarized in Table 1.

Example 5

A solution of butylethylmagnesium in isohexane (20.6 g, 20%) was analyzed for chloride (1350 ppm), and then the solution was transferred into a pressure-rated bottle equipped with a magnetic stir bar, a pressure gauge, and a thermocouple. The bottle was placed in a mineral oil bath. While stirring, solid Na (0.056 g) was added to the butylethylmagnesium solution. The solution was gradually heated to 99° C. (1.5 hours), and maintained at 99° C. for 50 minutes. The heating was then stopped, and the solution was allowed to cool, with stirring. During the heating, the pressure in the bottle increased to 52 psig (4.6×10⁵ Pa). A sample was removed from the bottle, and observed to be cloudy. The solution from the bottle was then filtered. The filtrate was analyzed for Cl$^\ominus$ content. The initial Mg to Al mole ratio was 20.1:1 (5.0 mole % Al); the final Mg to Al mole ratio was 46.4:1 (2.2 mole % Al). In the final solution, the amount of Na was 4 ppm. Conditions and results are summarized in Table 1.

Example 6

A solution of butylethylmagnesium in isohexane (15.0 g, 20%) was found to contain 1135 ppm of Cl$^\ominus$, 17.0 mg Cl, 0.48 mmol). Sodium on silica was prepared by stirring molten sodium with silica for 15-20 minutes. The sodium on silica (0.054 g, 20 wt % Na, 10.8 mg Na, 0.47 mmol Na) was added the butylethylmagnesium solution with stirring, and stirred overnight. The solution was filtered through a 0.2 micron PTFE filter membrane. The clear filtrate was analyzed, and found to contain 130 ppm Cl$^\ominus$. Conditions and results are summarized in Table 1.

TABLE 1

| Ex. | Mole ratio Na:Cl$^\ominus$ | Sample form | Temp. | Initial Cl$^\ominus$ | Final Cl$^\ominus$ | Reduction of Cl$^\ominus$ |
|---|---|---|---|---|---|---|
| 1 | 0.9:1$^a$ | slurry | 50° C. | 964 ppm | 617 ppm | 36% |
| 2 | 3.3:1$^b$ | slurry | 22° C. | 1177 ppm | 876 ppm | 25.6% |
| 3 | 1.3:1 | solution | 22° C. | 616 ppm | 442 ppm | 28.2% |
| 4 | 3:1 | solution | 22° C. | 1350 ppm | 10 ppm | 99.6% |
| 5 | 3:1 | solution | 99° C. | 1350 ppm | <5 ppm | 99.6% |
| 6 | 1:1 | solution | 22° C. | 1135 ppm | 130 ppm | 88.5% |

$^a$Ten percent of the weight of the slurry was excluded from the calculation of this ratio because it was assumed that the solids were ten percent of the slurry weight.
$^b$Twenty percent of the weight of the slurry was excluded from the calculation of this ratio because it was assumed that the solids were twenty percent of the slurry weight.

Example 7

A solution of butylethylmagnesium in a mixture of isohexane and heptane (170 g, 20%) was analyzed for chloride (841 ppm). Hyflo (10.8 g), followed by NaK (0.22 g, 44:56 Na:K wt/wt; moles of alkali metal:Cl$^\ominus$=1.85:1) were added to the butylethylmagnesium solution, and this mixture was stirred for one hour at ambient conditions. The mixture was filtered twice through the same filter screen, using 15-40 psig (2.05×10⁵ to 3.77×10 Pa) pressure. After 102 g of filtrate were collected and removed, a slurry of butylethylmagnesium in heptane (150 g, 20%), estimated to contain 1000 ppm chloride ion, having had Hyflo (2.4 g) added to the slurry, was added to the filter, now coated with the Hyflo from the filtration of the NaK-treated solution. Another 56 g of filtrate were collected and removed; this filtrate was combined with the 102 g filtrate, and the combined filtrate was analyzed for chloride ion. The cake on the filter screen was slightly sticky. Conditions and results are summarized in Table 2.

Example 8

A slurry of butylethylmagnesium in isohexane (~246 g, ~20 wt %) was estimated to contain approximately, by weight, 20% solids (predominantly magnesium chloride) and also estimated to have 1000-1100 ppm (0.20-0.22 g, 5.6-6.2 mmol) dissolved Cl$^\ominus$. This slurry was treated at ~22° C. with 0.33 g of NaK (44:56 wt/wt, 11 mmol). The slurry was stirred for 3.5 hours, then 4.7 g of Hyflo was added, and the slurry was shaken well. Hyflo (9.8 g) was suspended in isohexane, poured into the Mott filter assembly, and filtered using a slight pressure (5 psi, 3.4×10⁴ Pa) of N$_2$. The filtrate contained some Hyflo, and was poured back into the filter. The process was repeated 3-4 times to ensure a good pre-coat had been set and the filtrate was clear. The butylethylmagnesium slurry was then filtered through the pad of Hyflo. Approximately 136 g of clear solution were collected. The Cl$^\ominus$ content was 730 ppm; the Al content was 4.35 mole %, relative to Mg. Conditions and results are summarized in Table 2.

Example 9

A small amount of triethylaluminum (0.55 g) was added to a slurry of butylethylmagnesium in heptane (125.5 g, 20%). A portion of the slurry (15 g) was removed and analyzed for chloride (930 ppm). Another 10 g of the slurry was removed. The remainder of the slurry was transferred to a 3-necked round-bottom flask which had a stir bar in it. The slurry was heated at 45° C. for one hour, allowed to cool, and a 12 g sample was removed and found to contain 814 ppm chloride. Hyflo (1.6 g) was added to the slurry. The remainder of the samples sent for analysis were returned to the slurry. While stirring at 36° C., NaK (0.68 g, 44:56 Na:K wt/wt) was added to the slurry; the temperature of the slurry was raised to 45° C., and the slurry temperature increased to 52° C. The temperature was brought down to 43-48° C. by removing the heating mantle, and the temperature was kept in this range, with stirring, for one hour. A mixture of Hyflo (10.8 g) and a solution of butylethylmagnesium in heptane (87.1 g, 20%) was prepared and filtered, to coat the filter screen. The filtrate was removed. The butylethylmagnesium slurry was filtered through the coated filter screen; a sample of this filtrate was analyzed for chloride (322 ppm). The initial Mg to Al mole ratio was estimated to be 25:1 (4 mole % Al); the final Mg to Al mole ratio was 33.1:1 (3 mole % Al). In the final solution, the amount of Na was 1.1 ppm; the amount of K was less than 0.1 ppm. Conditions and results are summarized in Table 2.

Example 10

A slurry of butylethylmagnesium in isohexane (184 g, 19.5 wt %) having an initial Al content of 4.72 mole % relative to Mg and containing approximately 1400 ppm of Cl$^\ominus$ (256 mg Cl$^\ominus$, 7.2 mmol Cl$^\ominus$) was added to a 44:56 wt/wt alloy of NaK (2.1 g, 70.3 mmol). The slurry was heated to 45° C., and stirred at 45° C. for 3.5 hours. The slurry was then filtered at 45° C. through a pad of Hyflo (9.8 g) prepared as described in Example 9. The chloride ion levels had been reduced to 806 ppm; the final Al content had been reduced to 4.25 mole % relative to Mg. The Mg and butylethylmagnesium amounts remained virtually unchanged. Conditions and results are summarized in Table 2.

Example 11

This Example was similar to Example 10, except that the initial Al content was 0.22 wt % and 4.72 mole % relative to Mg, while the Mg content was 4.26 wt %; the butylethylmagnesium was 19.4 wt % of the slurry. The NaK-treated slurry was stirred for 4.5 hours at 22° C. and filtered at 22° C. Also, 2.8 g of Hyflo were added to the slurry, and the slurry was shaken well, then filtered through a pad of Hyflo (9.5 g) prepared as described in Example 9. The Cl$^\ominus$ content had been reduced to 206 ppm. The final Al content was 0.07 wt % and 1.56 mole % relative to Mg; the final Mg content was 4.11 wt %, and the final butylethylmagnesium concentration was 18.7 wt %. Conditions and results are summarized in Table 2.

Example 12

A solution of butylethylmagnesium in isohexane (15.0 g, 19.6 wt %) containing 1040 ppm of $Cl^{\ominus}$ (15.6 mg Cl, 0.44 mmol) was added to a 44:56 wt/wt alloy of sodium and potassium (NaK; 15 mg, 0.50 mmol). This mixture was stirred overnight, and filtered to give a clear solution containing <15 ppm $Cl^{\ominus}$. Conditions and results are summarized in Table 2.

Example 13

Hyflo (10.8 g) and NaK (0.48 g, 22:78 Na:K wt/wt) were added with stirring to a solution of butylethylmagnesium in isohexane (100 g, 21.6%, 1065 ppm $Cl^{\ominus}$). A solution of butylethylmagnesium in isohexane (51 g, 21.6%, 1065 ppm $Cl^{\ominus}$) and a solution of butylethylmagnesium in heptane (19 g, 20%, 701 ppm $Cl^{\ominus}$) were added to the NaK-treated solution; the resultant solution weighed 170 g, and had a chloride ion content of 1024 ppm (for this solution, the alkali metal:$Cl^{\ominus}$ ratio was 2.9:1). This first solution was stirred for an hour, and filtered, pre-coating a filter screen. A solution of butylethyl-mag-nesium in heptane (200 g, 20%, 701 ppm $Cl^{\ominus}$) was filtered through the coated filter screen. The combined filtrates were recycled twice through the filter; 150 g of filtrate were collected and removed.

Meanwhile, a slurry of butylethylmagnesium in isohexane (325 g, 20%, 1073 ppm $Cl^{\ominus}$) had 5.4 g of Hyflo added to it; this slurry was heated to 45° C. for about an hour. This second slurry was then filtered through the same coated filter screen. During the filtration, 208 g of filtrate were collected and removed. This 208 g filtrate portion was combined with the 150 g filtrate portion; the combined filtrate was analyzed (91 ppm chloride ion). Filtration of the slurry continued, and a second filtrate portion was collected and analyzed (337 ppm chloride ion). The initial Mg to Al mole ratio was 27.4:1 (3.6 mole % Al); the final Mg to Al mole ratio was 30.9:1 (3.2 mole % Al). In the final solution, the amount of Na was 2.0 ppm; the amount of K was 1.2 ppm. Conditions and results are summarized in Table 2.

Example 14

A filter screen was pre-coated with a solution containing 4.3 g of Hyflo in a butylethylmagnesium solution in heptane (50 g, 20%, estimated to contain 1400 ppm $Cl^{\ominus}$). The filtrate (33 g) was recovered and combined with a solution of butyl-ethyl-magnesium in heptane (215 g, 20%; estimated 1400 ppm $Cl^{\ominus}$) to make a solution weighing 240 g. A small amount of triethylaluminum (0.19 g) was added to the combined solution. NaK (0.28 g, 22:78 Na:K wt/wt; moles of alkali metal:$Cl^{\ominus}$=~1:1) and Hyflo (8.6 g) were added to the butyl-ethylmagnesium solution. The solution was stirred for one hour, and then filtered through the pre-coated filter screen. The filtrate was analyzed for chloride ion and for sodium and potassium. The initial Mg to Al mole ratio was 70.9:1 (1.4 mole % Al); the final Mg to Al mole ratio was 69.4:1 (1.4 mole % Al). In the final solution, the amount of Na was 9.4 ppm; the amount of K was 10.2 ppm; after sitting overnight, the amount of Na was 1.9 ppm; the amount of K was 7.5 ppm. Conditions and results are summarized in Table 2.

TABLE 2

| Ex. | Mole ratio alkali metal:$Cl^{\ominus a}$ | Sample form | Temp | Initial $Cl^{\ominus}$ | Final $Cl^{\ominus}$ | Reduction of $Cl^{\ominus}$ |
|---|---|---|---|---|---|---|
| 7 | $1.85:1^b$ $0.9:1^c$ | solution + slurry | room | 841 ppm | 514 ppm | $38.9\%^d$ |
| 8 | ~2:1 | slurry | 22° C. | 1100 $ppm^d$ | 730 ppm | 33.6% |
| 9 | 7.6:1 | slurry | 52° C. | 930 ppm | 332 ppm | 64.3% |
| 10 | ~10:1 | slurry | 45° C. | 1400 $ppm^d$ | 806 ppm | 42.4% |
| 11 | ~10:1 | slurry | 22° C. | 1400 $ppm^d$ | 206 ppm | 85.3% |
| 12 | 1.14:1 | solution | 22° C. | 1040 ppm | <15 ppm | 98.6% |
| 13 | $2.9:1^b$ $0.93:1^c$ | solution + slurry | | 1024 ppm 1073 $ppm^e$ | 91 $ppm^f$ 337 $ppm^e$ | $91.1\%^f$ $68.6\%^e$ |
| 14 | ~1:1 | solution | | 1400 $ppm^d$ | 171 ppm | 87.8% |

$^a$The mole ratio is calculated using the total of the moles of potassium and sodium.
$^b$This value is the ratio for the initial solution.
$^c$This ratio accounts for the overall amount of chloride ion in the filtrate that was analyzed.
$^d$This is an estimated value.
$^e$This is the value for the second portion, which was not stirred with NaK.
$^f$This value is for the combined filtrate, part of which was stirred with NaK.

Comparative Example 1

Hyflo (3.3 g) was added to a slurry of butylethylmagnesium in isohexane (184 g, 19.4%), and the slurry was shaken well. There were 8.9 g of Hyflo as a filter pad on the filter, prepared as in Example 8. The butylethylmagnesium slurry was filtered through the Hyflo filter pad with a slight pressure of nitrogen (10-15 psi, $6.9 \times 10^4$ to $1.03 \times 10^5$ Pa). Approximately 69 g of solution were collected. The $Cl^{\ominus}$ content was determined to be 976 ppm; the Al content was 4.72 mole %, relative to Mg.

Comparative Example 2

In order to determine the composition of the precipitate formed by the presence of soluble halide, a solution of butyl-ethylmagnesium in isohexane (20%) containing triethylaluminum (mole ratio Mg:Al=4.5) which had not been treated with an alkali metal was allowed to stand for about six months. At the end of the six-month period, the solid that had formed was collected and analyzed. Table 3 summarizes the results determined by methods other than NMR; Table 4 summarizes the $^1$H NMR results. As can be seen from the results below, approximately 95% of the material is made up of three components: EtMgCl, BuMgCl, and HMgCl. Expressing these components in terms of $MgCl_2$, $MgH_2$, and MgBuEt gives the formula $(MgCl_2)_{0.475}(MgH_2)_{0.35}(MgBuEt)_{0.125}$.

TABLE 3

| Substance | Mg | Al | Cl⊖ | H$_2$* | Butane* | Ethane* |
|---|---|---|---|---|---|---|
| Measured | 35.5% | 0.43% | 41.31% | 12.1 mmol/g solid | 0.43 mmol/g solid | 0.94 mmol/g solid |
| Calculated | | | | | 1.21% | 2.5% |

*Determined by gas evolution.

TABLE 4

| Compound | Amount | Amount |
|---|---|---|
| EtMgCl | 19.63 wt % | 16.17 mol % |
| BuMgCl | 14.83 wt % | 9.26 mol % |
| (AlEt$_3$)$_2$•MgEt$_2$ | 2.58 wt % | 0.55 mol % |
| HMgCl | 58.26 wt % | 70.43 mol % |
| Mg(CH=CHR)$_2$ | 0.71 wt % | 0.27 mol % |
| Isohexane | 3.49 wt % | 2.94 mol % |
| MgCl$_2$ | 0.49 wt % | 0.38 mol % |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

The invention claimed is:

1. A process for reducing an initial amount of soluble halide in a solution comprising a liquid organic medium, at least one viscosity reducing agent, at least one dihydrocarbylmagnesium compound, and the initial amount of soluble halide, which process comprises mixing at least one alkali metal with said solution at a mole ratio of alkali metal to magnesium of less than about 1:2.5, thereby forming precipitated soluble halides.

2. A process according to claim 1 wherein the mole ratio of alkali metal to said initial amount of soluble halide is no more than about 10:1.

3. A process according to claim 1 wherein said alkali metal is sodium or sodium potassium alloy.

4. A process according to claim 1 wherein said alkali metal is on a support material, and wherein said support material is silica, alumina, silica-alumina, or diatomaceous earth.

5. A process according to claim 1 wherein said liquid organic medium is a saturated hydrocarbon, and wherein said saturated hydrocarbon is isopentane, hexane, isohexane, or heptane.

6. A process according to claim 1 wherein said liquid organic medium is an aromatic hydrocarbon, and wherein said aromatic hydrocarbon is toluene.

7. A process according to claim 1 wherein said dihydrocarbylmagnesium compound is n-butylethylmagnesium or n-butyloctylmagnesium.

8. A process according to claim 1 wherein said soluble halide is reduced by at least about 25%.

9. A process according to claim 1 wherein said viscosity reducing agent is a trihydrocarbylaluminum compound.

10. A process according to claim 1 wherein a filter aid is used, and wherein said filter aid is diatomaceous earth, charcoal, or activated carbon.

11. A process according to claim 1 wherein the mole ratio of alkali metal to soluble halide is at least about 0.75:1, wherein said viscosity reducing agent is a trihydrocarbylaluminum compound, and wherein the amount of said trihydrocarbylaluminum compound in the solution is reduced.

12. A process according to claim 1 wherein, after reduction of soluble halide and separation of precipitated soluble halides, less than about 50 ppm of alkali metal is present in the solution.

13. A process according to claim 1 wherein said alkali metal is sodium or sodium potassium alloy; wherein said liquid organic medium is hexane, isohexane, heptane, or toluene; wherein said dihydrocarbylmagnesium compound is n-butylethylmagnesium or n-butyloctylmagnesium; and wherein the mole ratio of alkali metal to soluble halide is in the range of about 0.5:1 to about 5:1.

14. A process according to claim 13 wherein a filter aid is used, and wherein said filter aid is diatomaceous earth, charcoal, or activated carbon.

15. A process according to claim 13 wherein the sodium or sodium potassium alloy is on a support material, and wherein said support material is silica, alumina, silica-alumina, or diatomaceous earth.

16. A process according to claim 13 wherein said viscosity reducing agent is a trihydrocarbylaluminum compound.

17. A process for reducing an initial amount of soluble halide in a slurry comprising a liquid organic medium, at least one viscosity reducing agent, at least one dihydrocarbylmagnesium compound, solids from the formation of said dihydrocarbylmagnesium compound, and the initial amount of soluble halide, which process comprises mixing at least one alkali metal with said slurry at a mole ratio of alkali metal to magnesium of less than about 1:1.25, thereby forming precipitated soluble halides.

18. A process according to claim 17 wherein the mole ratio of alkali metal to said initial amount of soluble halide is no more than about 20:1.

19. A process according to claim 17 wherein the mole ratio of alkali metal to soluble halide is at least about 7.5:1, wherein said viscosity reducing agent is a trihydrocarbylaluminum compound, and wherein the amount of said trihydrocarbylaluminum compound in the solution is reduced.

20. A process according to claim 17 wherein said alkali metal is sodium or sodium potassium alloy; wherein said liquid organic medium is hexane, isohexane, or heptane; wherein said dihydrocarbylmagnesium compound is n-butylethylmagnesium or n-butyloctylmagnesium; and wherein the mole ratio of alkali metal to soluble halide is in the range of about 6:1 to about 12:1.

21. A process which comprises
   a) forming, in a liquid organic medium, at least one dihydrocarbylmagnesium compound from at least one hydrocarbyl halide and magnesium metal, wherein optionally at least one viscosity reducing agent is present, resulting in a slurry comprising said liquid organic medium, said dihydrocarbylmagnesium compound, solids from the formation of said dihydrocarbylmagnesium compound, and an initial amount of soluble halide;
   b) removing said solids from at least a portion of said slurry formed in a), resulting in a solution comprising said liquid organic medium, said dihydrocarbylmagnesium compound, and said initial amount of soluble halide; and
   c) reducing the initial amount of soluble halide in at least a portion of said solution formed in b), in which at least one viscosity reducing agent is present, by mixing at least one alkali metal with said solution at a mole ratio of alkali metal to magnesium of less than about 1:2.5, thereby forming precipitated soluble halides.

22. A process according to claim 21 wherein the mole ratio of alkali metal to said initial amount of soluble halide is no more than about 10:1.

23. A process according to claim 21 wherein said alkali metal is sodium or sodium potassium alloy.

24. A process according to claim 21 wherein said alkali metal is on a support material, and wherein said support material is silica, alumina, silica-alumina, or diatomaceous earth.

25. A process according to claim 21 wherein said liquid organic medium is a saturated hydrocarbon, and wherein said saturated hydrocarbon is isopentane, hexane, isohexane, or heptane.

26. A process according to claim 21 wherein said alkali metal is sodium or sodium potassium alloy, and wherein said dihydrocarbylmagnesium compound is n-butylethylmagnesium or n-butyloctylmagnesium.

27. A process according to claim 21 wherein said soluble halide is reduced by at least about 25%.

28. A process according to claim 21 wherein a viscosity reducing agent is present in a).

29. A process according to claim 21 wherein a filter aid is used, and wherein said filter aid is diatomaceous earth, charcoal, or activated carbon.

30. A process according to claim 21 wherein the mole ratio of alkali metal to soluble halide is at least about 0.75:1, wherein a viscosity reducing agent is present in a), wherein said viscosity reducing agent is a trihydrocarbylaluminum compound, and wherein the amount of said trihydrocarbylaluminum compound in the solution is reduced.

31. A process according to claim 21 wherein, after reduction of soluble halide and separation of precipitated soluble halides, less than about 50 ppm of alkali metal is present in the solution.

32. A process according to claim 21 wherein said alkali metal is sodium or sodium potassium alloy; wherein said liquid organic medium is hexane, isohexane, or heptane; wherein said dihydrocarbylmagnesium compound is n-butylethylmagnesium or n-butyloctylmagnesium; and wherein the mole ratio of alkali metal to soluble halide is in the range of about 0.5:1 to about 5:1.

33. A process according to claim 32 wherein a filter aid is used, and wherein said filter aid is diatomaceous earth, charcoal, or activated carbon.

34. A process according to claim 32 wherein the sodium or sodium potassium alloy is on a support material, and wherein said support material is silica, alumina, silica-alumina, or diatomaceous earth.

35. A process according to claim 32 wherein a viscosity reducing agent is present in a).

36. A process which comprises
   i) forming, in a liquid organic medium, at least one dihydrocarbylmagnesium compound from at least one hydrocarbyl halide and magnesium metal, wherein optionally at least one viscosity reducing agent is present, resulting in a slurry comprising said liquid organic medium, said dihydrocarbylmagnesium compound, solids from the formation of said dihydrocarbylmagnesium compound, and an initial amount of soluble halide; and
   ii) reducing the initial amount of soluble halide in at least a portion of said slurry formed in i), in which at least one viscosity reducing agent is present, by mixing at least one alkali metal with said slurry at a mole ratio of alkali metal to magnesium of less than about 1:1.25, thereby forming precipitated soluble halides.

37. A process according to claim 36 wherein the mole ratio of alkali metal to said initial amount of soluble halide is no more than about 20:1.

38. A process according to claim 36 wherein the mole ratio of alkali metal to soluble halide is at least about 7.5:1, wherein said viscosity reducing agent is a trihydrocarbylaluminum compound, and wherein the amount of said trihydrocarbylaluminum compound in the solution is reduced.

39. A process according to claim 36 wherein said alkali metal is sodium or sodium potassium alloy; wherein said liquid organic medium is hexane, isohexane, or heptane; wherein said dihydrocarbylmagnesium compound is n-butylethylmagnesium or n-butyloctylmagnesium; and wherein the mole ratio of alkali metal to soluble halide is in the range of about 6:1 to about 12:1.

* * * * *